US012594115B2

(12) United States Patent
Leung et al.

(10) Patent No.: US 12,594,115 B2
(45) Date of Patent: Apr. 7, 2026

(54) LACERATION SYSTEM AND DEVICE, AND METHODS FOR LACERATION

(71) Applicant: Boston Scientific Medical Device Limited, Galway (IE)

(72) Inventors: Jackie Leung, Richmond Hill (CA); Eduardo Moriyama, Richmond (CA); Gareth Davies, Toronto (CA); Kaylie Lau, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 678 days.

(21) Appl. No.: 17/905,982

(22) PCT Filed: Mar. 15, 2021

(86) PCT No.: PCT/IB2021/052142
§ 371 (c)(1),
(2) Date: Sep. 9, 2022

(87) PCT Pub. No.: WO2021/186329
PCT Pub. Date: Sep. 23, 2021

(65) Prior Publication Data
US 2023/0165627 A1 Jun. 1, 2023

Related U.S. Application Data

(60) Provisional application No. 62/992,250, filed on Mar. 20, 2020.

(51) Int. Cl.
*A61B 18/14* (2006.01)
*A61B 18/12* (2006.01)
*A61B 18/00* (2006.01)

(52) U.S. Cl.
CPC ...... *A61B 18/1477* (2013.01); *A61B 18/1206* (2013.01); *A61B 2018/00369* (2013.01); *A61B 2018/00577* (2013.01)

(58) Field of Classification Search
CPC . A61B 18/1206; A61B 18/14; A61B 18/1477; A61B 18/1492;
(Continued)

(56) References Cited

U.S. PATENT DOCUMENTS

| | | | |
|---|---|---|---|
| 175,254 A | 3/1876 | Oberly | |
| 827,626 A | 7/1906 | Gillet | |

(Continued)

FOREIGN PATENT DOCUMENTS

| | | |
|---|---|---|
| WO | 2005/048861 A1 | 6/2005 |
| WO | 2019/109013 A1 | 6/2019 |

OTHER PUBLICATIONS

International Search Report and Written Opinion received for PCT Patent Application No. PCT/IB2021/052142, mailed on Jun. 15, 2021, 7 pages.

*Primary Examiner* — Michael F Peffley
(74) *Attorney, Agent, or Firm* — Nelson Mullins Riley & Scarborough LLP

(57) ABSTRACT

A laceration device for use in medical procedures includes a shaft having a proximal portion defining a proximal end, and an opposed distal portion defining a distal end. A perforation electrode is at the distal end, and a first electrical connector extends proximally from the perforation electrode for connection to a power source. An outwardly extending barb is positioned proximal of the distal end. The barb has an inner end proximate the shaft and an outer end opposite the inner end. A laceration electrode is proximal of and adjacent the inner end of the barb, and a second electrical connector extends proximally from the laceration electrode for connection to the power source.

20 Claims, 7 Drawing Sheets

(58) Field of Classification Search
CPC .. A61B 2017/0412; A61B 2018/00267; A61B 2018/00357; A61B 2018/00369; A61B 2018/00571; A61B 2018/00577; A61B 2018/00601; A61B 2018/126; A61B 2018/1407; A61B 2018/1425; A61B 2018/144; A61B 2018/1475; A61B 2090/036; A61B 2090/374
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,660,571 A * | 4/1987 | Hess ................ A61B 18/1492 606/49 |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |

(56)                    References Cited

U.S. PATENT DOCUMENTS

| | | | |
|---|---|---|---|
| 6,360,128 | B2 | 3/2002 | Kordis et al. |
| 6,364,877 | B1 | 4/2002 | Goble et al. |
| 6,385,472 | B1 | 5/2002 | Hall et al. |
| 6,394,976 | B1 | 5/2002 | Winston et al. |
| 6,395,002 | B1 | 5/2002 | Ellman et al. |
| 6,419,674 | B1 | 7/2002 | Bowser et al. |
| 6,428,551 | B1 | 8/2002 | Hall et al. |
| 6,450,989 | B2 | 9/2002 | Dubrul et al. |
| 6,475,214 | B1 | 11/2002 | Moaddeb |
| 6,485,485 | B1 | 11/2002 | Winston et al. |
| 6,508,754 | B1 | 1/2003 | Liprie et al. |
| 6,524,303 | B1 | 2/2003 | Garibaldi |
| 6,530,923 | B1 | 3/2003 | Dubrul et al. |
| 6,554,827 | B2 | 4/2003 | Chandrasekaran et al. |
| 6,562,031 | B2 | 5/2003 | Chandrasekaran et al. |
| 6,562,049 | B1 | 5/2003 | Norlander et al. |
| 6,565,562 | B1 | 5/2003 | Shah et al. |
| 6,607,529 | B1 | 8/2003 | Jones et al. |
| 6,632,222 | B1 | 10/2003 | Edwards et al. |
| 6,639,999 | B1 | 10/2003 | Cookingham et al. |
| 6,650,923 | B1 | 11/2003 | Lesh et al. |
| 6,651,672 | B2 | 11/2003 | Roth |
| 6,662,034 | B2 | 12/2003 | Segner et al. |
| 6,663,621 | B1 | 12/2003 | Winston et al. |
| 6,702,811 | B2 | 3/2004 | Stewart et al. |
| 6,709,444 | B1 | 3/2004 | Makower |
| 6,723,052 | B2 | 4/2004 | Mills |
| 6,733,511 | B2 | 5/2004 | Hall et al. |
| 6,740,103 | B2 | 5/2004 | Hall et al. |
| 6,752,800 | B1 | 6/2004 | Winston et al. |
| 6,755,816 | B2 | 6/2004 | Ritter et al. |
| 6,811,544 | B2 | 11/2004 | Schaer |
| 6,814,733 | B2 | 11/2004 | Schwartz et al. |
| 6,820,614 | B2 | 11/2004 | Bonutti |
| 6,834,201 | B2 | 12/2004 | Gillies et al. |
| 6,842,639 | B1 | 1/2005 | Winston et al. |
| 6,852,109 | B2 | 2/2005 | Winston et al. |
| 6,855,143 | B2 | 2/2005 | Davison et al. |
| 6,860,856 | B2 | 3/2005 | Ward et al. |
| 6,869,431 | B2 | 3/2005 | Maguire et al. |
| 6,911,026 | B1 | 6/2005 | Hall et al. |
| 6,951,554 | B2 | 10/2005 | Johansen et al. |
| 6,951,555 | B1 | 10/2005 | Suresh et al. |
| 6,955,675 | B2 | 10/2005 | Jain |
| 6,970,732 | B2 | 11/2005 | Winston et al. |
| 6,980,843 | B2 | 12/2005 | Eng et al. |
| 7,029,470 | B2 | 4/2006 | Francischelli et al. |
| 7,056,294 | B2 | 6/2006 | Khairkhahan et al. |
| 7,083,566 | B2 | 8/2006 | Tornes et al. |
| 7,097,643 | B2 * | 8/2006 | Cornelius ......... A61M 25/0068 |
| | | | 606/41 |
| 7,112,197 | B2 | 9/2006 | Hartley et al. |
| 7,335,197 | B2 | 2/2008 | Sage et al. |
| 7,618,430 | B2 | 11/2009 | Scheib |
| 7,651,492 | B2 | 1/2010 | Wham |
| 7,666,203 | B2 | 2/2010 | Chanduszko et al. |
| 7,678,081 | B2 | 3/2010 | Whiting et al. |
| 7,682,360 | B2 | 3/2010 | Guerra |
| 7,828,796 | B2 | 11/2010 | Wong et al. |
| 7,900,928 | B2 | 3/2011 | Held et al. |
| 7,938,826 | B2 * | 5/2011 | Davis ................. A61B 17/0057 |
| | | | 606/41 |
| 8,192,425 | B2 | 6/2012 | Mirza et al. |
| 8,221,405 | B2 * | 7/2012 | Whisenant ............ A61B 5/053 |
| | | | 606/41 |
| 8,257,323 | B2 | 9/2012 | Joseph et al. |
| 8,388,549 | B2 | 3/2013 | Paul et al. |
| 8,500,697 | B2 | 8/2013 | Kurth et al. |
| 11,339,579 | B1 | 5/2022 | Stearns |
| 2001/0012934 | A1 | 8/2001 | Chandrasekaran et al. |
| 2001/0021867 | A1 | 9/2001 | Kordis et al. |
| 2002/0019644 | A1 | 2/2002 | Hastings et al. |
| 2002/0022781 | A1 | 2/2002 | McIntire et al. |
| 2002/0022836 | A1 | 2/2002 | Goble et al. |
| 2002/0035361 | A1 | 3/2002 | Houser et al. |

| | | | |
|---|---|---|---|
| 2002/0087153 | A1 | 7/2002 | Roschak et al. |
| 2002/0087156 | A1 | 7/2002 | Maguire et al. |
| 2002/0111618 | A1 | 8/2002 | Stewart et al. |
| 2002/0123749 | A1 | 9/2002 | Jain |
| 2002/0147485 | A1 | 10/2002 | Mamo et al. |
| 2002/0169377 | A1 | 11/2002 | Khairkhahan et al. |
| 2002/0188302 | A1 | 12/2002 | Berg et al. |
| 2002/0198521 | A1 | 12/2002 | Maguire |
| 2003/0032929 | A1 | 2/2003 | McGuckin |
| 2003/0040742 | A1 | 2/2003 | Underwood et al. |
| 2003/0144605 | A1 | 7/2003 | Burbank et al. |
| 2003/0144658 | A1 | 7/2003 | Schwartz et al. |
| 2003/0158480 | A1 | 8/2003 | Tornes et al. |
| 2003/0163153 | A1 | 8/2003 | Scheib |
| 2003/0225392 | A1 | 12/2003 | McMichael et al. |
| 2004/0015162 | A1 | 1/2004 | McGaffigan |
| 2004/0024396 | A1 | 2/2004 | Eggers |
| 2004/0030328 | A1 | 2/2004 | Eggers et al. |
| 2004/0044350 | A1 | 3/2004 | Martin et al. |
| 2004/0073243 | A1 | 4/2004 | Sepetka et al. |
| 2004/0077948 | A1 | 4/2004 | Molante et al. |
| 2004/0116851 | A1 | 6/2004 | Johansen et al. |
| 2004/0127963 | A1 | 7/2004 | Uchida et al. |
| 2004/0133113 | A1 | 7/2004 | Krishnan |
| 2004/0133130 | A1 | 7/2004 | Ferry et al. |
| 2004/0143256 | A1 | 7/2004 | Bednarek |
| 2004/0147950 | A1 | 7/2004 | Mueller et al. |
| 2004/0181213 | A1 | 9/2004 | Gondo |
| 2004/0230188 | A1 | 11/2004 | Cioanta et al. |
| 2005/0004585 | A1 | 1/2005 | Hall et al. |
| 2005/0010208 | A1 | 1/2005 | Winston et al. |
| 2005/0049628 | A1 | 3/2005 | Schweikert et al. |
| 2005/0059966 | A1 | 3/2005 | McClurken et al. |
| 2005/0065507 | A1 | 3/2005 | Hartley et al. |
| 2005/0085806 | A1 | 4/2005 | Auge et al. |
| 2005/0096529 | A1 | 5/2005 | Cooper et al. |
| 2005/0101984 | A1 | 5/2005 | Chanduszko et al. |
| 2005/0119556 | A1 | 6/2005 | Gillies et al. |
| 2005/0137527 | A1 | 6/2005 | Kunin |
| 2005/0149012 | A1 | 7/2005 | Penny et al. |
| 2005/0203504 | A1 | 9/2005 | Wham et al. |
| 2005/0203507 | A1 | 9/2005 | Truckai et al. |
| 2005/0261607 | A1 | 11/2005 | Johansen et al. |
| 2005/0288631 | A1 | 12/2005 | Lewis et al. |
| 2006/0041253 | A1 | 2/2006 | Newton et al. |
| 2006/0074398 | A1 | 4/2006 | Whiting et al. |
| 2006/0079769 | A1 | 4/2006 | Whiting et al. |
| 2006/0079787 | A1 | 4/2006 | Whiting et al. |
| 2006/0079884 | A1 | 4/2006 | Manzo et al. |
| 2006/0085054 | A1 | 4/2006 | Zikorus et al. |
| 2006/0089638 | A1 | 4/2006 | Carmel et al. |
| 2006/0106375 | A1 | 5/2006 | Werneth et al. |
| 2006/0135962 | A1 | 6/2006 | Kick et al. |
| 2006/0142756 | A1 | 6/2006 | Davies et al. |
| 2006/0189972 | A1 | 8/2006 | Grossman |
| 2006/0241586 | A1 | 10/2006 | Wilk |
| 2006/0247672 | A1 | 11/2006 | Vidlund et al. |
| 2006/0264927 | A1 | 11/2006 | Ryan |
| 2006/0276710 | A1 | 12/2006 | Krishnan |
| 2007/0060879 | A1 | 3/2007 | Weitzner et al. |
| 2007/0066975 | A1 | 3/2007 | Wong et al. |
| 2007/0118099 | A1 | 5/2007 | Trout, III |
| 2007/0123964 | A1 | 5/2007 | Davies et al. |
| 2007/0167775 | A1 | 7/2007 | Kochavi et al. |
| 2007/0208256 | A1 | 9/2007 | Marilla |
| 2007/0225681 | A1 | 9/2007 | House |
| 2007/0270791 | A1 | 11/2007 | Wang et al. |
| 2008/0039865 | A1 | 2/2008 | Shaher et al. |
| 2008/0042360 | A1 | 2/2008 | Veikley |
| 2008/0086120 | A1 | 4/2008 | Mirza et al. |
| 2008/0097213 | A1 | 4/2008 | Carlson et al. |
| 2008/0108987 | A1 | 5/2008 | Bruszewski et al. |
| 2008/0146918 | A1 | 6/2008 | Magnin et al. |
| 2008/0171934 | A1 | 7/2008 | Greenan et al. |
| 2008/0208121 | A1 | 8/2008 | Youssef et al. |
| 2008/0275439 | A1 | 11/2008 | Francischelli et al. |
| 2009/0105742 | A1 | 4/2009 | Kurth et al. |
| 2009/0138009 | A1 | 5/2009 | Viswanathan et al. |
| 2009/0163850 | A1 | 6/2009 | Betts et al. |

(56)  References Cited

U.S. PATENT DOCUMENTS

| | | | |
|---|---|---|---|
| 2009/0177114 A1 | 7/2009 | Chin et al. | |
| 2009/0264977 A1 | 10/2009 | Bruszewski et al. | |
| 2010/0042195 A1 | 2/2010 | Cooke et al. | |
| 2010/0087789 A1 | 4/2010 | Leeflang et al. | |
| 2010/0125282 A1 | 5/2010 | Machek et al. | |
| 2010/0168684 A1 | 7/2010 | Ryan | |
| 2010/0179632 A1 | 7/2010 | Bruszewski et al. | |
| 2010/0191142 A1 | 7/2010 | Paul et al. | |
| 2010/0194047 A1 | 8/2010 | Sauerwine | |
| 2011/0046619 A1 | 2/2011 | Ducharme | |
| 2011/0152716 A1 | 6/2011 | Chudzik et al. | |
| 2011/0160592 A1 | 6/2011 | Mitchell | |
| 2011/0166569 A1 | 7/2011 | Whayne et al. | |
| 2011/0190763 A1 | 8/2011 | Urban et al. | |
| 2012/0232546 A1 | 9/2012 | Mirza et al. | |
| 2012/0265055 A1 | 10/2012 | Melsheimer et al. | |
| 2012/0330156 A1 | 12/2012 | Brown et al. | |
| 2013/0184551 A1 | 7/2013 | Paganelli et al. | |
| 2013/0184735 A1 | 7/2013 | Fischell et al. | |
| 2013/0282084 A1 | 10/2013 | Mathur et al. | |
| 2014/0206987 A1 | 7/2014 | Urbanski et al. | |
| 2014/0296769 A1 | 10/2014 | Hyde et al. | |
| 2016/0008058 A1* | 1/2016 | Hu ......................... | A61B 18/02 606/41 |
| 2016/0220741 A1 | 8/2016 | Garrison et al. | |
| 2017/0258521 A1 | 9/2017 | Asirvatham et al. | |
| 2017/0333116 A1* | 11/2017 | Lee ..................... | A61B 18/1477 |
| 2019/0021763 A1 | 1/2019 | Zhou et al. | |
| 2019/0247035 A1 | 8/2019 | Gittard et al. | |
| 2019/0374281 A1* | 12/2019 | Davies ............... | A61B 18/1482 |
| 2021/0077186 A1* | 3/2021 | Pate ................... | A61B 17/0057 |

* cited by examiner

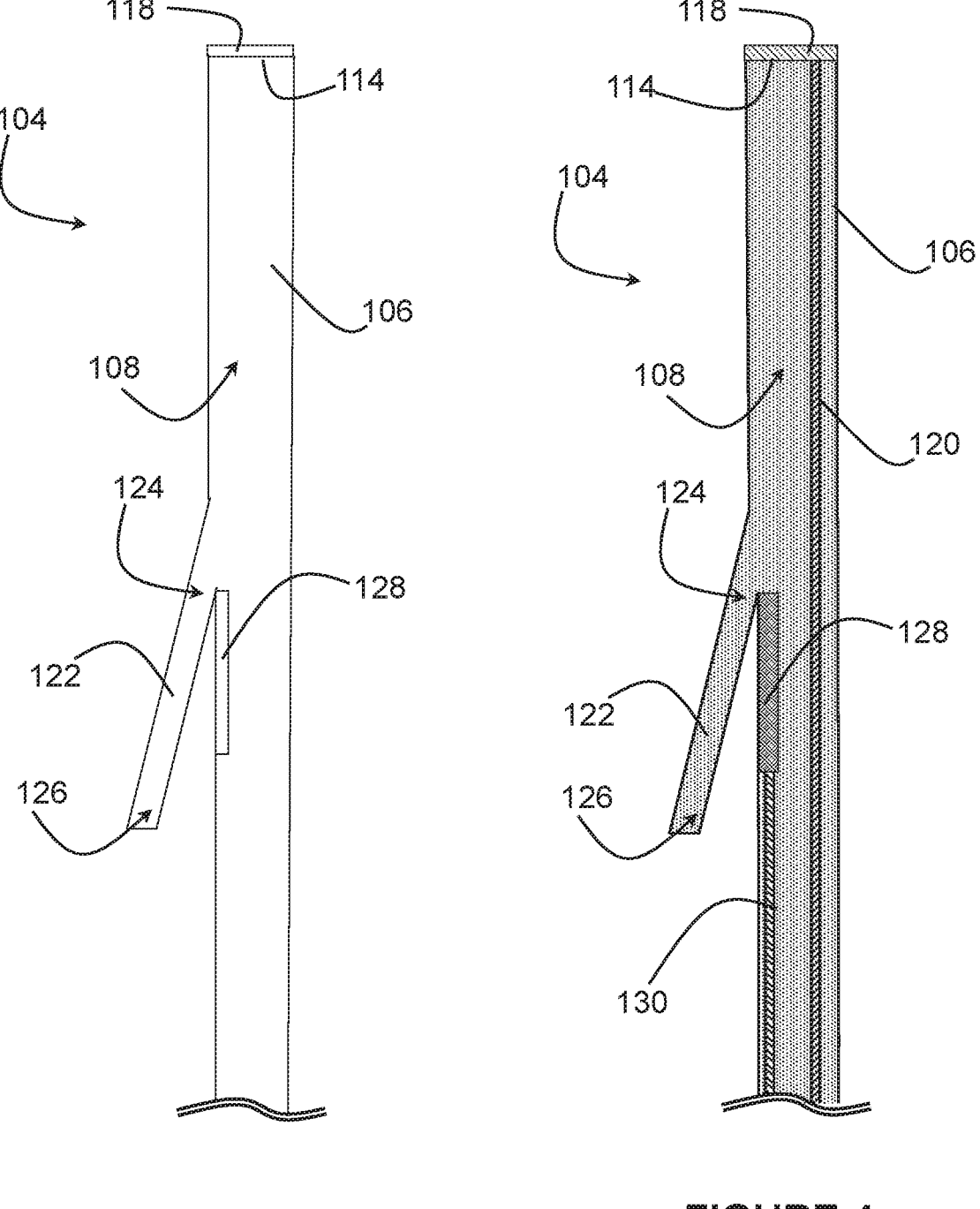
FIGURE 3          FIGURE 4

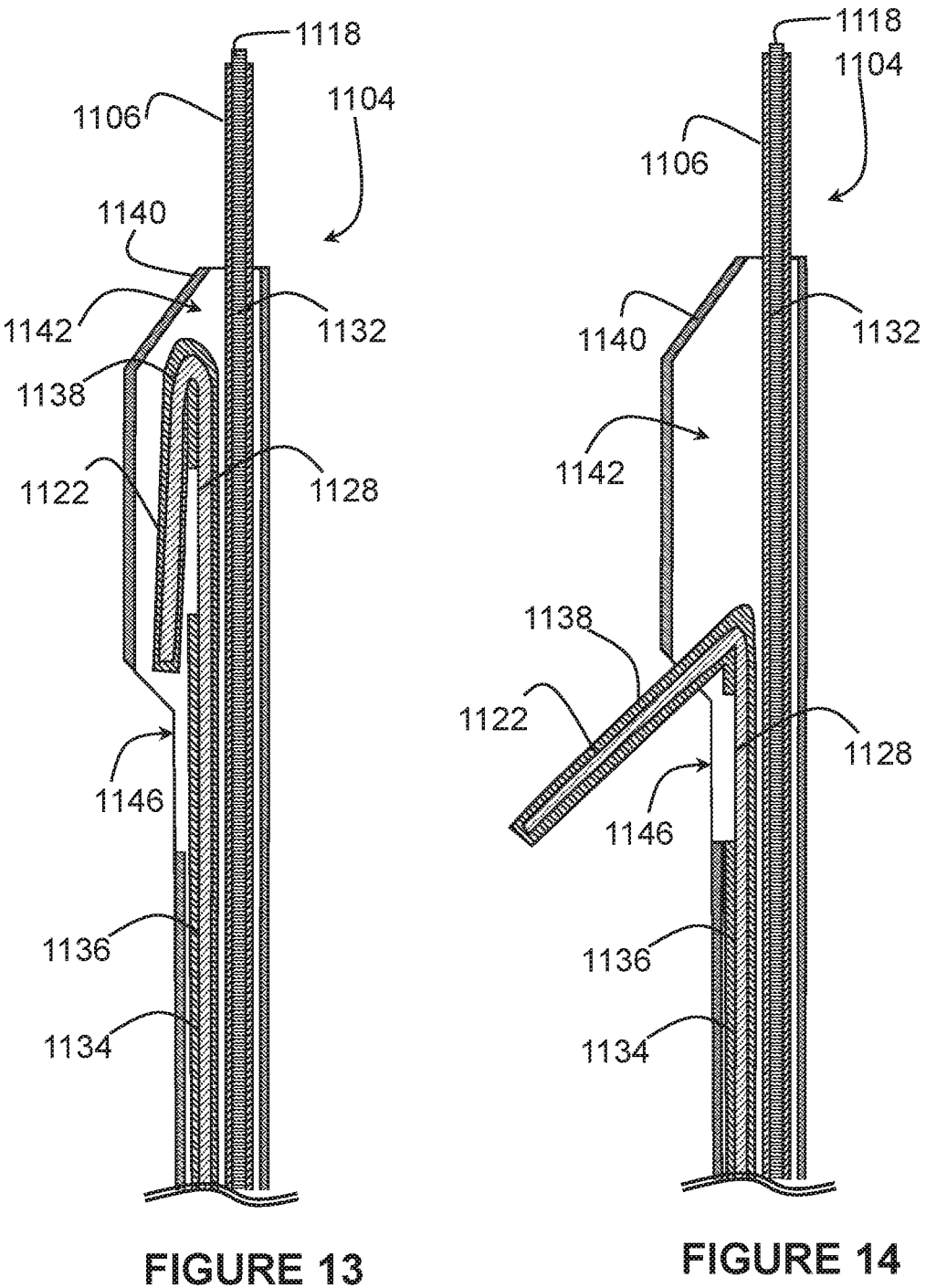
FIGURE 13            FIGURE 14

LACERATION SYSTEM AND DEVICE, AND METHODS FOR LACERATION

FIELD

This document relates to medical procedures that involve laceration of an anatomical structure. More specifically, this document relates to devices for laceration, and related systems and methods.

SUMMARY

The following summary is intended to introduce the reader to various aspects of the detailed description, but not to define or delimit any invention.

Laceration devices for use in medical procedures are disclosed. According to some aspects, a laceration device for use in medical procedures includes a shaft having a proximal portion defining a proximal end, and an opposed distal portion defining a distal end. A perforating tip is at the distal end. An outwardly extending barb is positioned proximally of the distal end. The barb has an inner end proximate the shaft and an outer end opposite the inner end. A laceration electrode is proximal of and adjacent the inner end of the barb, and an electrical connector extends proximally from the laceration electrode for connection to a power source In some examples, the laceration device further includes a handle connected to the proximal end of the shaft. The handle can include a control for manipulating the barb.

In some examples, the barb is integral with the shaft. The shaft and the barb can be formed from an electrically insulative material.

In some examples, the perforating tip includes a perforation electrode, and the device includes another electrical connector extending proximally from the perforation electrode for connection to the power source. The electrical connectors can be in the form of wires that are embedded in the electrically insulative material of the shaft.

In some examples, the barb is movable between a deployed position in which the outer end is moved radially outwardly from the shaft, and a collapsed position in which the outer end is moved radially towards the shaft. The barb can be biased towards the deployed position. The device can further include a retainer for retaining the barb in the collapsed position.

In some examples, the laceration device includes a first insulated wire forming the shaft, and a second insulated wire. The second insulated wire can be crimped to define a first section extending along the first insulated wire, and a second section extending radially outwardly from the first portion and forming the barb. The laceration electrode can be positioned at the crimp. The retainer can include a sheath housing at least a portion of the first insulated wire and at least a portion of the first section of the second insulated wire. When in the collapsed position, the second section of the second insulated wire can be housed within the sheath, and when in the deployed position, the second section of the second insulated wire can be outside of the sheath. The barb can be movable from the collapsed position to the deployed position by sliding the second insulated wire proximally relative to the sheath.

Methods for creating lacerations are also disclosed. According to some aspects, a method for creating a laceration includes a. advancing a perforating tip of a laceration device towards a proximal surface of a target anatomical structure; b. advancing the perforating tip to perforate the target anatomical structure; c. advancing the laceration device to position the perforating tip beyond a distal surface of the target anatomical structure and to pass a barb of the laceration device through the perforation; d. retracting the laceration device to abut the barb with the distal surface of the target anatomical structure and position a laceration electrode of the laceration device in contact with the target anatomical structure; and e. with the barb abutting the distal surface of the target anatomical structure, activating the laceration electrode of the laceration device applying force to the laceration device to lacerate the target anatomical structure.

In some examples, the perforating tip includes a perforation electrode, step b. includes supplying RF energy to the perforation electrode, and step e. includes supplying RF energy to the laceration electrode.

In some examples, between step c. and step d., the method further includes moving the barb from a collapsed position to a deployed position. Moving the barb from the collapsed position to the deployed position can include moving the barb radially outwardly from the laceration electrode. Moving the barb from the collapsed position to the deployed position can include sliding the barb proximally with respect to the perforating tip. The barb can be biased towards the deployed position, and during steps a. to c., the barb can be held in the collapsed position. Moving the barb from the collapsed position to the deployed position can include releasing the hold on the barb.

In some examples, the target anatomical structure is a valve leaflet.

Laceration systems for use in medical procedures are also disclosed. According to some aspects, a laceration system includes an RF generator, and a laceration device. The laceration device includes a shaft. The shaft has a proximal portion defining a proximal end, and an opposed distal portion defining a distal end. A perforating tip is at the distal end. An outwardly extending barb is positioned proximal of the distal end. The barb has an inner end proximate the shaft and an outer end opposite the inner end. A laceration electrode is proximal of and adjacent the inner end of the barb. The laceration electrode is electrically connectable to the RF generator.

BRIEF DESCRIPTION OF THE DRAWINGS

The accompanying drawings are for illustrating examples of articles, methods, and apparatuses of the present disclosure and are not intended to be limiting. In the drawings:

FIG. 3 is an enlarged front view of a portion of the laceration device of FIG. 1;

FIG. 4 is a cross-section taken through the portion of the laceration device shown in FIG. 3;

FIG. 13 is a cross-section taken through the laceration device as shown in FIG. 11; and FIG. 14 is a cross-section taken through the laceration device as shown in FIG. 12.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are devices, and related systems and methods, that can be used in medical procedures in which a target anatomical structure is lacerated. Such medical procedures can include transvenous structural heart procedures, which can involve the laceration of soft tissue. Such soft tissue can include, for example, a valve leaflet or an atrial septum. The devices disclosed herein can be an "all-in-one" device that can perforate the target anatomical structure (e.g. the valve leaflet), anchor to the target anatomical structure, and then lacerate the target anatomical structure. This can reduce the complexity of such procedures, and reduce the number of devices required for such procedures.

Figure 1:
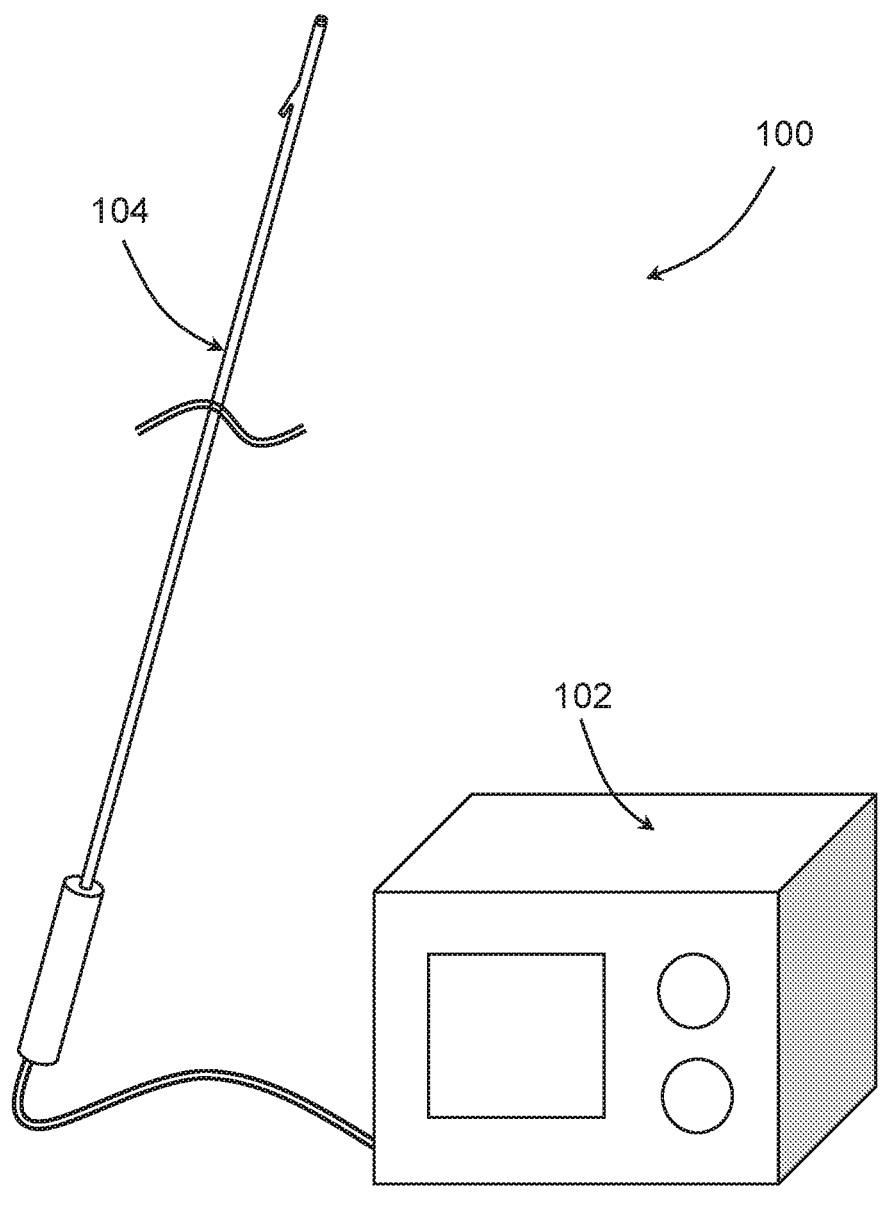
FIG. 1 is a perspective view of an example laceration system.

Referring now to FIG. 1, an example laceration system 100 is shown. The system 100 includes a power source in the form of a radiofrequency (RF) generator 102, as well as a laceration device 104. The laceration device 104 is electrically connectable to the RF generator 102, to supply RF energy to electrodes (described below) of the laceration device 104. The system can also include one or more grounding pads (not shown) connected to the RF generator 102 for operation in monopolar mode (if operation is in bipolar mode, the grounding pad can be omitted and a return electrode can be added). The system 100 may further include an electro-anatomical mapping (EAM) monitoring system (not shown) electrically connectable to the laceration device 104 to monitor advancement of the perforating tip of the laceration device towards a proximal surface of the anatomical structure 202 and to confirm perforation of the target anatomical structure 200. The position of the perforating tip can be confirmed using EAM system.

Figure 2:
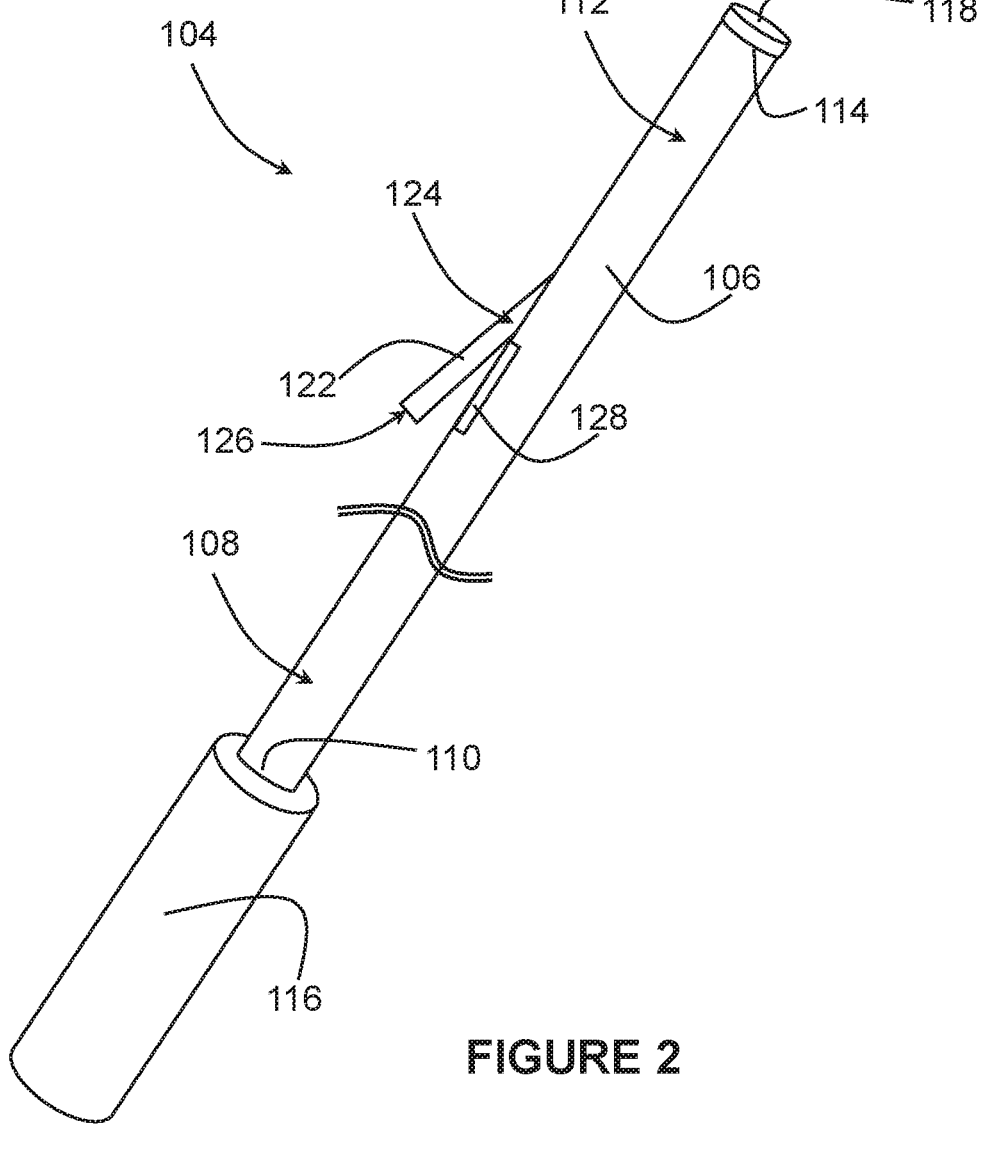
FIG. 2 is a perspective view of the laceration device of FIG. 1.

Referring to FIG. 2, in the example shown, the laceration device 104 includes a shaft 106, which has a proximal portion 108 defining a proximal end 110 and a distal portion 112 defining a distal end 114. A handle 116 is connected to the proximal end 110 of the shaft 106. The handle can optionally include various controls (not shown), e.g. for controlling delivery of RF energy from the generator or for manipulating a barb of the device (described below). The shaft can be of various constructions. For example, the shaft can be in the form of an insulated wire, as described below, or can be a plastic tube that houses various other components of the device.

Referring to FIGS. 3 and 4, the laceration device 104 includes a perforating tip. In the example shown, the perforating tip is in the form of a perforation electrode 118, which is positioned at the distal end 114 of the shaft 106. A first electrical connector 120 extends proximally from the perforation electrode 118, for connection to the RF generator 102. In alternative examples, the perforating tip can be of another configuration, e.g. it can be configured for mechanical perforation.

Referring still to FIGS. 3 and 4, in the example shown, the laceration device 104 further includes an outwardly extending barb 122, which extends outwardly from the shaft 106 and is positioned proximally of the distal end 114 of the shaft 106. The barb 122 has an inner end 124 that is proximate the shaft 106, and an outer end 126 opposite the inner end 124. In the example shown, the inner end 124 is joined to and integral with the shaft 106; however, in alternative examples, the inner end can be proximate to but separated from the shaft 106, or joined to the shaft in a non-integral fashion.

Figure 5:
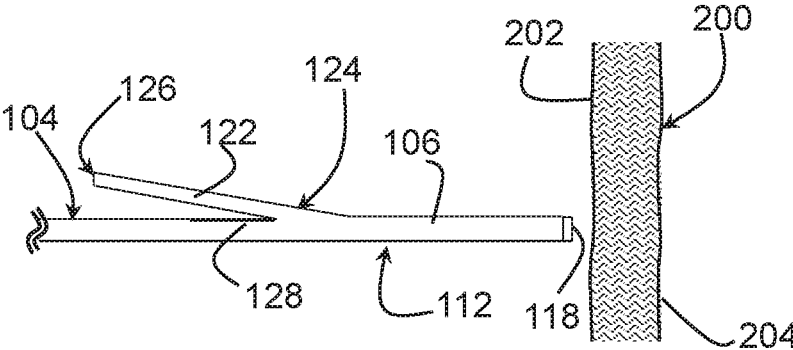
FIG. 5 is a schematic view showing a first step of a method for creating a laceration.
Figure 6:
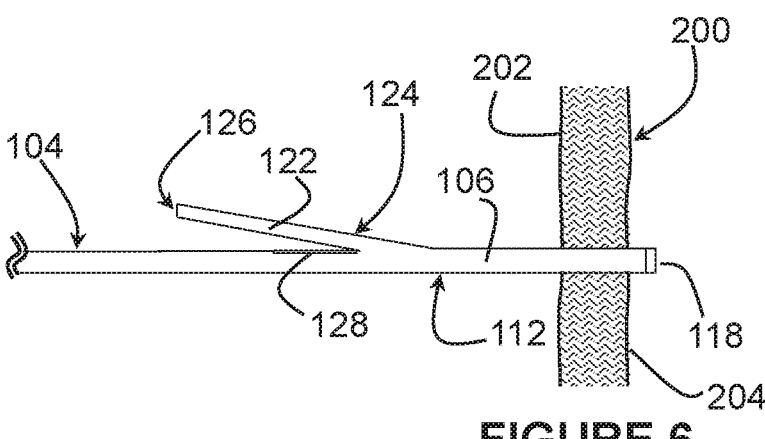
FIG. 6 is a schematic view showing a second step of the method of FIG. 5.
Figure 7:
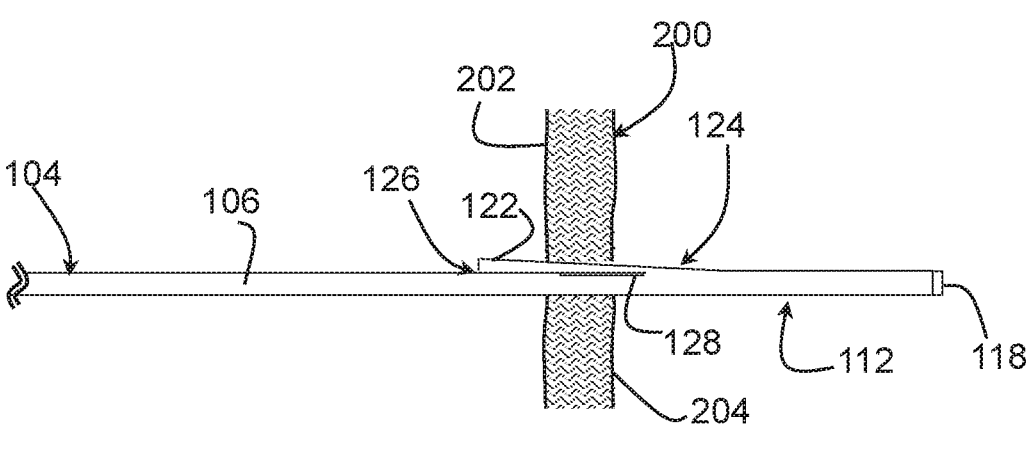
FIG. 7 is a schematic view showing a third step of the method of FIGS. 5 and 6.
Figure 8:
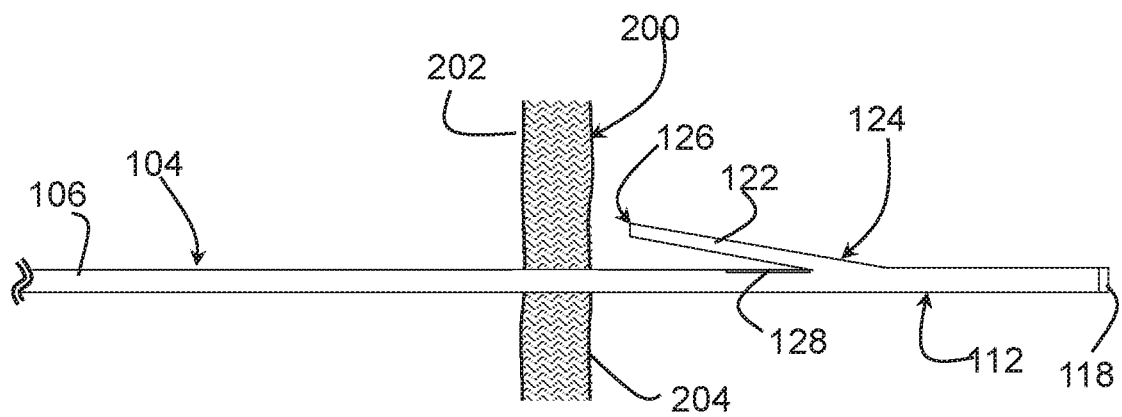
FIG. 8 is a schematic view showing a fourth step of the method of FIGS. 5 to 7.
Figure 9:
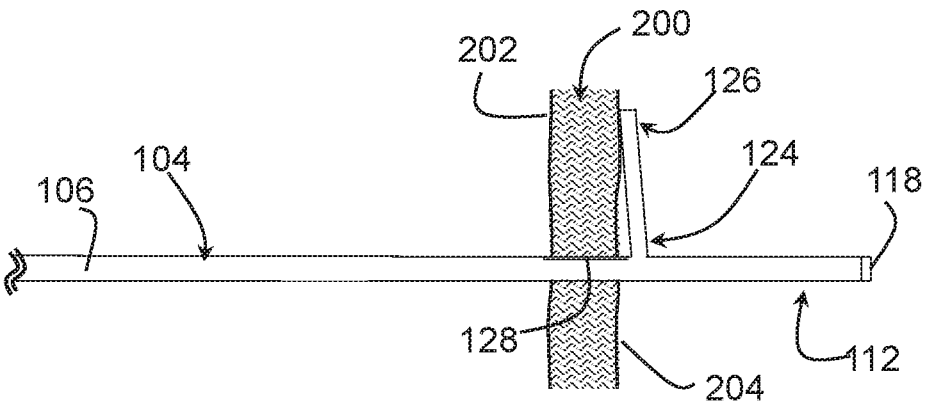
FIG. 9 is a schematic view showing a fifth step of the method of FIGS. 5 to 8.
Figure 10:
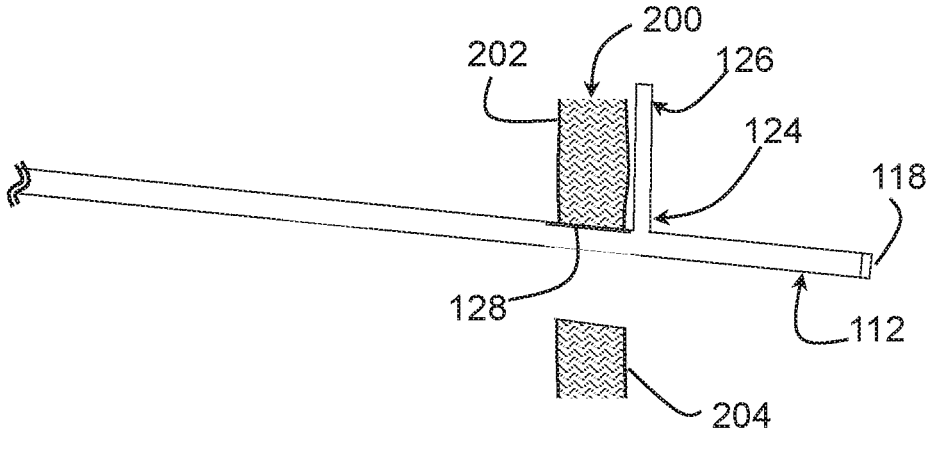
FIG. 10 is a schematic view showing a sixth step of the method of FIGS. 5 to 9.

In the example shown, the barb 122 is biased towards the position shown in FIGS. 5, 6 and 8, referred to as a "deployed position", in which the outer end 126 is spaced radially from the shaft 106, and the barb 122 is inclined with respect to the shaft 106, so that the outer end 126 is positioned proximally of the inner end 124. As shown in FIG. 7, upon the application of force (e.g. by an anatomical structure 200 such as a valve leaflet), the barb 122 can collapse towards the shaft 106, to a "collapsed position". Upon the application of force in the opposite direction (e.g. by the anatomical structure 200), the barb 122 can flex to move the outer end 126 further radially outwardly to an "engaged position", as shown in FIGS. 9 and 10; however, the barb 122 is configured to resist movement of the outer end 126 beyond the engaged position, so that when in the configuration shown in FIGS. 9 and 10, the barb 122 prevents or resists proximal movement of the laceration device 104.

In alternative examples, the barb may not flex to an engaged position. Instead, barb may move only between the deployed and collapsed positions, and may be sufficiently stiff to resist further movement. Such examples may be particularly useful in examples where the device is used to lacerate tissues that are relatively movable, such as valve leaflets, as the application of force to the device may be undesirable as it may cause the tissue to move.

Referring back to FIGS. 3 and 4, the laceration device 104 further includes a laceration electrode 128. The laceration electrode 128 is positioned proximal of and adjacent the inner end 124 of the barb 122. When the barb 122 is in the position shown in FIG. 9 and is abutting a surface of the anatomical structure 200, the laceration electrode 128 is in contact with the anatomical structure 200. A second electrical connector 130 extends proximally from the laceration electrode 128, for connection to the RF generator 102.

As mentioned above, the laceration electrode 128 is positioned proximal of and adjacent the inner end 124 of the barb 122. In the example shown, wherein the barb is configured to flex to the engaged position, the laceration electrode 128 is positioned in the crook of the barb 122, so that it is positioned to contact the anatomical structure 200 when the barb 122 is in the engaged position and abutting the surface of the anatomical structure 200. In alternative examples, wherein the barb does not flex to an engaged position, the laceration electrode can be positioned proximal of and adjacent the inner end of the barb, but can be slightly proximal of the position shown in FIGS. 3 and 4, so that when the outer end of the barb is in contact with the surface of the anatomical structure, the laceration electrode is in contact with the anatomical structure.

Referring still to FIGS. 3 and 4, in the example shown, the barb 122 is integral with the shaft 106. That is, in the example shown, the shaft 106 and the barb 122 are both formed from an electrically insulative material. The first electrical connector 120 is in the form of a first wire that is embedded in the electrically insulative material of the shaft 106, and the second electrical connector 130 is in the form of a second wire that is embedded in the electrically insulative material of the shaft 106. The perforation electrode 118 and laceration electrode 128 can be formed by exposed ends of the first and second wires, respectively, or can be separate metallic pieces that are secured to the first and second wires, respectively, as shown.

While in the example shown the barb 122 includes a single elongate piece of material, in alternative examples, the barb can be of another configuration that allows for the barb to pass through the anatomical structure 200 and then anchor to the anatomical structure 200 to prevent proximal movement of the laceration device. For example, the barb can include two elongate pieces of material that are circumferentially spaced apart around the shaft, or can be configured similar to an umbrella that can be opened and closed.

In some examples (not shown), the barb can be radiopaque or can include a radiopaque marker, to allow for fluoroscopic visualization. Similarly, the barb can be echogenic or can include an echogenic marker, to allow for ultrasound visualization.

Referring now to FIGS. 5 to 10, in use, the laceration device 104 can be used to lacerate the target anatomical structure 200. Particularly, referring first to FIG. 5, the laceration device 104 can be advanced towards a proximal surface 202 of the target anatomical structure 200. Referring to FIG. 6, the perforation electrode 118 can then be activated (e.g. by supplying RF energy from the RF generator 102 to the perforation electrode 118) to perforate the target anatomical structure 200. Referring to FIGS. 7 and 8, the laceration device 104 can then be advanced, to position the perforation electrode 118 beyond a distal surface 204 of the target anatomical structure 200 and to pass the barb 122 through the perforation. As the barb 122 passes through the perforation, as shown in FIG. 7, it collapses from the deployed position to the collapsed position. When the barb 122 clears the target anatomical structure 122, it moves back to the deployed position, as shown in FIG. 8. The laceration device 104 can then be retracted, as shown in FIG. 9, to abut the barb 122 with the distal surface 204 of the target anatomical structure 200 and cause the barb 122 to flex towards the engaged position. In alternative examples, where the barb 122 is relatively stiff, rather than the barb 122 flexing to the engaged position, the barb can simply contact the distal surface of the target anatomical structure 200 and remain in the deployed position.

With the barb 122 in the position shown in FIG. 9, the laceration electrode 128 is in contact with the target anatomical structure 200, and the laceration electrode 128 can be activated (e.g. by supplying RF energy to the laceration electrode 128 from the RF generator 102). Referring to FIG.

10, with the laceration electrode 128 activated, force can be applied to the laceration device 104, to pull the laceration electrode 128 laterally, and lacerate the target anatomical structure 200. When laceration is complete, the laceration device 104 can be withdrawn from the target structure 200, by retracting the barb 122 and the perforation electrode 118 through the laceration.

In some examples, the areas around the perforation electrode 118 and laceration electrode 128 can be flushed with non-ionic fluid (e.g. a dextrose solution, saline, or a contrast solution) to act as an insulator. The device can be provided with various fluid lumens and fluid ports (not shown) to facilitate fluid delivery.

Referring now to FIGS. 11 to 14, another example of a laceration device is shown. In FIGS. 11 to 14, features that are similar to those of FIGS. 1 to 10 will be referred to with like reference numerals, incremented by 1000.

Figures 11, 12:
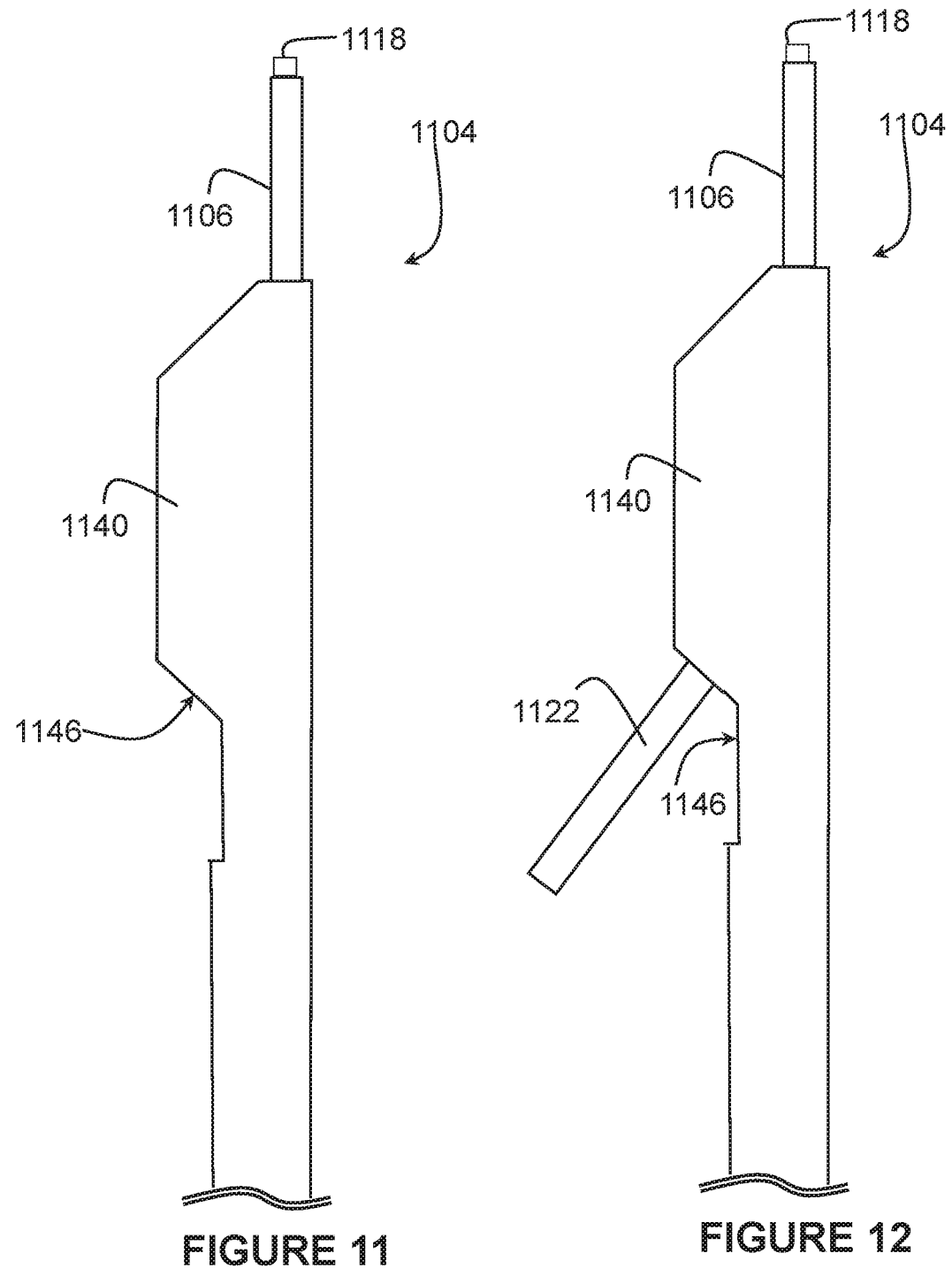
FIG. 11 is a front view of a portion of another example laceration device, with a barb thereof in a collapsed position.
FIG. 12 is a front view of the portion of the laceration device of FIG. 11, with the barb in a deployed position.

Referring to FIGS. 11 and 12, the laceration device 1104 is configured to allow for a user to move the barb 1122 from the collapsed position (shown in FIG. 11, in which the barb 1122 is not visible) to the deployed position (shown in FIG. 12), and vice versa, without relying on contact with an anatomical structure to do so. That is, the user can more readily control the position of the barb 1122. Particularly, referring to FIGS. 13 and 14, the laceration device 1104 includes a first insulated wire 1132, which forms the shaft 1106 of the laceration device 1104. An exposed tip of the insulated wire 1132 provides the perforation electrode 1118. The laceration device 1104 further includes a second insulated wire 1134, which provides the barb 1122. That is, the second insulated wire 1134 is crimped to define a first section 1136 that extends along the first insulated wire 1132, and a second section 1138 that extends radially outwardly from the first section 1136 and forms the barb 1122. Similarly to the device of FIGS. 1 to 10, the barb 1122 is biased towards the deployed position, shown in FIG. 14, and can be moved to the collapsed position, shown in FIG. 13, with the application of force. The barb 1122 can further be moved to an engaged position (not shown), which is similar to the engaged position of FIG. 9. An exposed section of the second insulated wire 1134 provides the laceration electrode 1128. Similarly to the device of FIGS. 1 to 10, the laceration electrode 1128 is positioned proximal of and adjacent the inner end of the barb 1122, generally at the position of the crimp and in the crook of the crimp.

Referring still to FIGS. 13 and 14, in the example shown, the laceration device further includes a retainer 1140 for retaining the barb 1122 in the collapsed position and selectively releasing the barb 1122 to the deployed position. In the example shown, the retainer 1140 is generally in the form of a sheath that has a lumen 1142. The sheath can be low-profile, to pass through a perforation. The retainer houses a portion of the first insulated wire 1132; however, the first insulated wire 1132 passes through the retainer 1140, so that the perforation electrode 1188 is outside of the lumen 1142. The retainer 1140 further houses the first section 1136 of the second insulated wire 1134. Furthermore, when in the collapsed position, the barb 1122 (i.e. the second section 1138 of the second insulated wire 1134) is also retained in the lumen 1142. The lumen 1142 has an opening 1146 at its proximal end. The position of the retainer 1140 is fixed with respect to the first insulated wire 1132. For example, both the retainer 1140 and the first insulated wire 1132 can be secured to the handle (not shown) of the laceration device 1104. However, the second insulated wire 1134 is movable distally and proximally with respect to the retainer 1140. When in the position shown in FIG. 13, the barb 1122 is housed within the lumen 1142 of the retainer 1140 and held in the collapsed position by the retainer 1140. As shown in FIG. 14, the second insulated wire 1134 can be slid proximally relative to the retainer 1140 (e.g. by pulling the proximal end of the second insulated wire through the handle, not shown) to move the barb 1122 through the opening 1146 and out of the retainer 1140, and thereby release the barb 1122 to the deployed position. To move the barb 1122 back to the collapsed position, the second insulated wire 1134 can be slid distally, back to the position shown in FIG. 13 (e.g. by pushing the proximal end of the second insulated wire through the handle, not shown). Sliding of the second insulated wire 1134 can optionally be done using a control such as a sliding switch, which can for example be provided on the handle.

The laceration device of FIGS. 11 to 14 can be used in a similar fashion to the laceration device of FIGS. 1 to 10; however, the position of the barb can be manually controlled by the user.

In any of the above examples, the device can be configured so that the delivery of RF energy is determined by the position of the barb. For example, the device can be configured so that when the barb is in the deployed position and RF energy is delivered, the RF energy is automatically directed to the laceration electrode; however when the barb is in the collapsed position and RF energy is automatically directed to the perforation electrode.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A laceration device for use in medical procedures, comprising:
a shaft, the shaft having a proximal portion defining a proximal end, and an opposed distal portion defining a distal end;
a perforating tip at the distal end;
an outwardly extending barb positioned proximal of the distal end, the barb having an inner end proximate the shaft and an outer end opposite the inner end, wherein the barb is movable between a deployed position in which the outer end is moved radially outwardly from the shaft, and a collapsed position in which the outer end is moved radially towards the shaft, the barb being biased towards the deployed position whereby the barb collapses from the deployed position to the collapsed position as the barb passes through an anatomical structure and moves back to the deployed position upon clearing the anatomical structure; and
a laceration electrode proximal of and adjacent the inner end of the barb, and an electrical connector extending proximally from the laceration electrode for connection to a power source;
wherein the barb is configured to flex to an engaged position when force is applied in a direction opposite to the collapsed position, the barb being configured to resist movement beyond the engaged position to prevent proximal movement of the laceration device when the outer end contacts a distal surface of an anatomical structure.

2. The laceration device of claim 1, further comprising a handle connected to the proximal end of the shaft, wherein the handle comprises a control for manipulating the barb.

3. The laceration device of claim 1, wherein the barb is integral with the shaft.

4. The laceration device of claim 1, wherein the perforating tip comprises a perforation electrode, and the device further comprises another electrical connector extending proximally from the perforation electrode for connection to the power source.

5. The laceration device of claim 4, wherein
the shaft and the barb are formed from an electrically insulative material;
the electrical connectors are in the form of wires that are embedded in the electrically insulative material of the shaft.

6. The laceration device of claim 1, wherein the barb is radiopaque, includes a radiopaque marker, echogenic, or includes an echogenic marker.

7. The laceration device of claim 6, wherein the laceration electrode and the perforation electrode are formed by exposed ends of the electrical connectors.

8. The laceration device of claim 7, further comprising a retainer for retaining the barb in the collapsed position.

9. The laceration device of claim 8, wherein:
the laceration device comprises a first insulated wire forming the shaft, and a second insulated wire,
the second insulated wire is crimped to define a first section extending along the first insulated wire, and a second section extending radially outwardly from the first portion and forms the barb.

10. The laceration device of claim 9, wherein the laceration electrode is positioned at the crimp.

11. The laceration device of claim 9, wherein the retainer comprises a sheath housing at least a portion of the first insulated wire and at least a portion of the first section of the second insulated wire, wherein when in the collapsed position, the second section of the second insulated wire is housed within the sheath, and when in the deployed position, the second section of the second insulated wire is outside of the sheath.

12. The laceration device of claim 11, wherein the barb is movable from the collapsed position to the deployed position by sliding the second insulated wire proximally relative to the sheath.

13. A method for creating a laceration, comprising:
a. advancing a perforating tip of a laceration device towards a proximal surface of a target anatomical structure, the laceration device comprising a first insulated wire forming a shaft and a second insulated wire crimped to define a first section extending along the first insulated wire and second section extending radially outwardly from the first section and forming a barb;
b. advancing the perforating tip to perforate the target anatomical structure;
c. advancing the laceration device to position the perforating tip beyond a distal surface of the target anatomical structure and to pass the barb of the laceration device through the perforation;
d. retracting the laceration device to abut the barb with the distal surface of the target anatomical structure and position a laceration electrode of the laceration device in contact with the target anatomical structure; and e. with the barb abutting the distal surface of the target anatomical structure, activating the laceration electrode of the laceration device applying force to the laceration device to lacerate the target anatomical structure.

14. The method of claim 13, wherein step b. comprises supplying RF energy to a perforation electrode of the perforating tip and step e. comprises supplying RF energy to the laceration electrode.

15. The method of claim 13, wherein between step c. and step d., the method further comprises moving the barb from a collapsed position to a deployed position.

16. The method of claim 15, wherein moving the barb from the collapsed position to the deployed position comprises moving the barb radially outwardly from the laceration electrode.

17. The method of claim 15, wherein moving the barb from the collapsed position to the deployed position comprises sliding the barb proximally with respect to the perforation electrode.

18. The method of claim 15, wherein the barb is biased towards the deployed position;

during steps a. to c., the barb is held in the collapsed position; and moving the barb from the collapsed position to the deployed position comprises releasing the hold on the barb.

19. The method of claim 13, wherein the target anatomical structure is a valve leaflet.

20. A laceration system for use in medical procedures, comprising:

an RF generator configured to selectively deliver RF energy to a perforation electrode for tissue perforation and to a laceration electrode for tissue laceration; and a laceration device, the laceration device comprising i) a shaft, the shaft having a proximal portion defining a proximal end, and an opposed distal portion defining a distal end, ii) a perforating tip at the distal end, iii) an outwardly extending barb positioned proximal of the distal end, the barb having an inner end proximate the shaft and an outer end opposite the inner end, wherein the barb is movable between a deployed position in which the outer end is moved radially outwardly from the shaft, and a collapsed position in which the outer end is moved radially towards the shaft, the barb being biased towards the deployed position whereby the barb collapses from the deployed position to the collapsed position as the barb passes through an anatomical structure and moves back to the deployed position upon clearing the anatomical structure and iv) a laceration electrode proximal of and adjacent the inner end of the barb, the laceration electrode electrically connectable to the RF generator.

* * * * *